United States Patent [19]

Kopera

[11] Patent Number: 5,119,671
[45] Date of Patent: Jun. 9, 1992

[54] METHOD FOR FLEXIBLE FUEL CONTROL

[75] Inventor: John J. C. Kopera, Rochester Hills, Mich.

[73] Assignee: Chrysler Corporation, Highland Park, Mich.

[21] Appl. No.: 667,843

[22] Filed: Mar. 12, 1991

[51] Int. Cl.$^5$ ............................................. G01M 15/00
[52] U.S. Cl. ..................... 73/116; 73/61.41; 324/655
[58] Field of Search ............... 73/61.1 R, 861.04, 116; 324/654, 655, 656, 675, 663; 336/69

[56] References Cited

U.S. PATENT DOCUMENTS

| | | | |
|---|---|---|---|
| 2,772,393 | 11/1956 | Davis | 324/655 X |
| 4,187,462 | 2/1980 | Haker et al. | 324/655 X |
| 4,945,863 | 8/1990 | Schmitz et al. | 73/61.1 R X |

Primary Examiner—Jerry W. Myracle
Attorney, Agent, or Firm—Mark P. Calcaterra

[57] ABSTRACT

A method of controlling preselected parameters in an engine powered by a fuel mixture of first and second liquids utilizes differing dielectric constants of the first and second liquids to alter the frequency of an oscillator using a tank circuit formed by an inductor coil immersed in the fuel mixture and the distributed capacitance of the coil. The frequency of the oscillator therefore can be used to determine the percentages in the fuel mixture of the first and second liquids. The percentages, in turn, are used to control the preselected engine parameters.

6 Claims, 6 Drawing Sheets

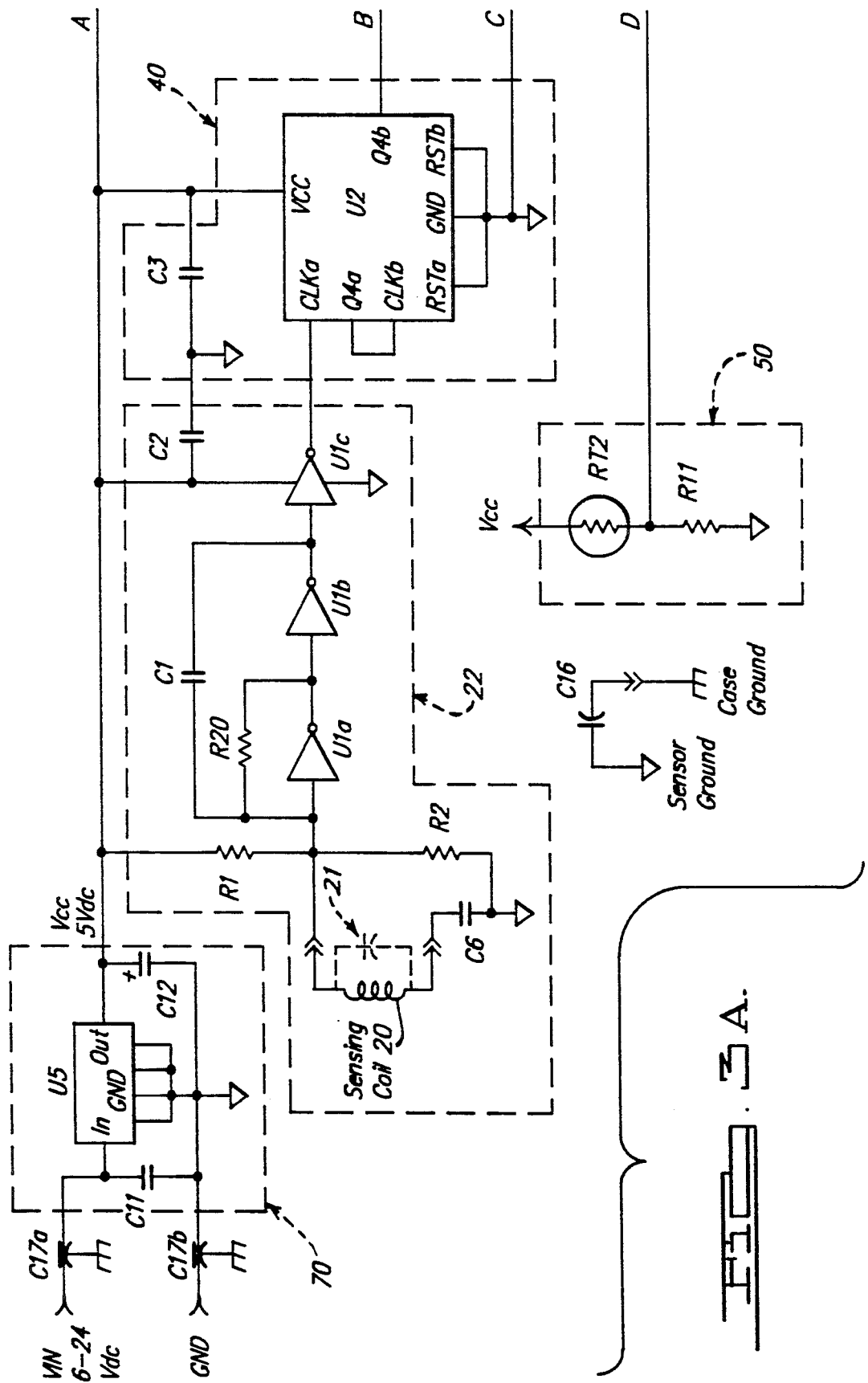

METHOD FOR FLEXIBLE FUEL CONTROL

BACKGROUND OF THE INVENTION

1. Field of the Invention

This invention relates to a method and apparatus for determining the percentage of two known liquids in a mixture where the two known liquids possess substantially different dielectric properties. The combined percentage of each of the two known liquids in a mixture is directly proportional to the distributed capacitance of an insulated wire coil immersed in the mixture.

2. Description of the Related Art

In the automotive industry there are demands for an automobile that can perform on both gasoline and alcohol. However, typical internal combustion engines must have selectively adjustable parameters, such as spark timing, for efficient combustion when running on the different fuels. One design that attempts to meet this demand is an optical refraction index sensor which utilizes the relationship between the percentage of alcohol in a fuel mixture and the angle of light refraction through the fuel mixture.

SUMMARY OF THE INVENTION

Due to shortages of oil and the promulgation of stringent emission standards, the automotive industry has been under intense pressure to develop internal combustion engines that can perform efficiently using alternative fuels such as methanol and ethanol. Currently, only methanol and ethanol are viable fuel alternatives to gasoline since both are able to create a similar amount of power in spark ignited engines.

In order to accommodate the fluctuating supply of alcohol based fuels, vehicle manufacturers have to modify their gasoline fuel systems to accept alcohol based fuels or gasoline/alcohol fuel mixtures. The subject invention is a method and apparatus for detecting the percentage of alcohol in a gasoline/alcohol mixture and relaying that information to an engine controller or microprocessor or other type of controller so that the spark timing and fuel ratio can be adjusted accordingly. Analogously, the subject invention also has the ability to detect the percentage of two known liquids (each of which may be a mixture itself) within a mixture wherein the liquids have substantially different dielectric properties.

The fuel mixture detection device of the subject invention consists of a coil which is immersed in the fuel mixture. A distributed capacitance is generated between the windings of the coil upon energization of the coil. The wire turns act as equivalent electrodes of a capacitor and the fuel mixture acts as a dielectric medium. This distributed capacitance of the coil is directly proportional to the dielectric constant of the mixture which, in turn, is directly proportional to the percentage of each fuel in the mixture. This assumes that the sensor is dealing with known fluids as a base (each of which could be a mixture of other fluids) so long as the two known fluids have significantly different dielectric constants. This distributed capacitance 21 is approximately represented by the equivalent circuit designated as a dashed line capacitor symbol and labeled $C_D$ as shown in FIG. 1 and in FIG. 3A.

The coil may be supported within a hollow casing defining a chamber. Interconnecting tubing is used to channel the liquid mixture to the coil within the chamber. An electrical circuit is interfaced with the coil and mounted immediately adjacent. In this manner, only the coil and the interconnections to the circuit are in contact with the liquid mixture. Without this type of arrangement, long interconnection cables would be needed which would undesirably add stray or parasitic impedance to the circuit thereby dwarfing the capacitance of the coil, rendering it a less accurate indicator of the liquid mixture flowing between the electrodes.

The circuit of the subject invention includes a unique oscillator utilizing the submerged coil. A relationship exists between the resonant frequency and the capacitance of the coil whereby the resonant frequency decreases as the capacitance of the coil increases. The dielectric constant of the mixture is determined by using the coil as the resonant element in the oscillator, thereby generating an oscillation frequency which is inverse proportionally related to the dielectric constant of the liquid mixture. The circuit then provides a means whereby the frequency is converted to a voltage output and sent to a controller for processing. In the case of a alcohol/gasoline fuel mixture for internal combustion engines, the output signal of the sensor is sent to an engine controller or computer means.

It is an object of the present invention to provide a method and apparatus for determining the percentage of two known liquids in a mixture where the two known liquids possess significantly different dielectric constants.

It is another object of the present invention to determine the percentage of alcohol in a gasoline/alcohol fuel mixture for use in selectively adjusting engine parameters.

It is yet another object of the present invention to utilize the relationship between the distributed capacitance of a coil and its resonant frequency to determine the percentage of two liquids in a mixture.

It is still another object of the present invention to represent the percentage of two known liquids in a mixture as a limited range voltage signal.

BRIEF DESCRIPTION OF THE DRAWINGS

Other objects, features and advantages of the present invention will become more fully apparent from the following detailed description of the preferred embodiment, the appended claims and in the accompanying drawings in which:

FIG. 3A is a schematic diagram of the circuitry of the flexible fuel system;

DETAILED DESCRIPTION OF THE PREFERRED EMBODIMENT

It is known that the electrical properties of gasoline differ considerably from those of methanol. One of those properties is of particular interest here, the dielectric constant of the two distinct liquids. More specifically, the dielectric constant of gasoline is approximately 2.05, whereas it is 32.63 (@25° C.) for methanol. Because of the order of magnitude of difference between the dielectric constant of the two fuels, the dielectric constant is a desirable property to sense for determining the relative percentage of gasoline and methanol in a mixture thereof.

A method of detecting this property is by measuring the change in distributed capacitance of a capacitor with the fuel mixture as its dielectric material. The measured capacitance is a direct indication of the composition of the mixture. Change in capacitance can be sensed as a change in the resonant frequency of a coil immersed in the mixture to be described in greater detail below. The resonant frequency is a function of the dielectric material and its value will change from its "air" value (i.e., where there is no dielectric material other than air) to some value dependent upon the fuel mixture's combined dielectric constant when the coil is immersed in the mixture. The subject invention senses the dielectric constant of the fuel mixture by using the distributed capacitance of a free-standing "air core" (dielectric material is air) inductor as a standard, comparing it with the distributed capacitance generated when a fuel mixture acts as the dielectric material instead of air.

Figure 1:
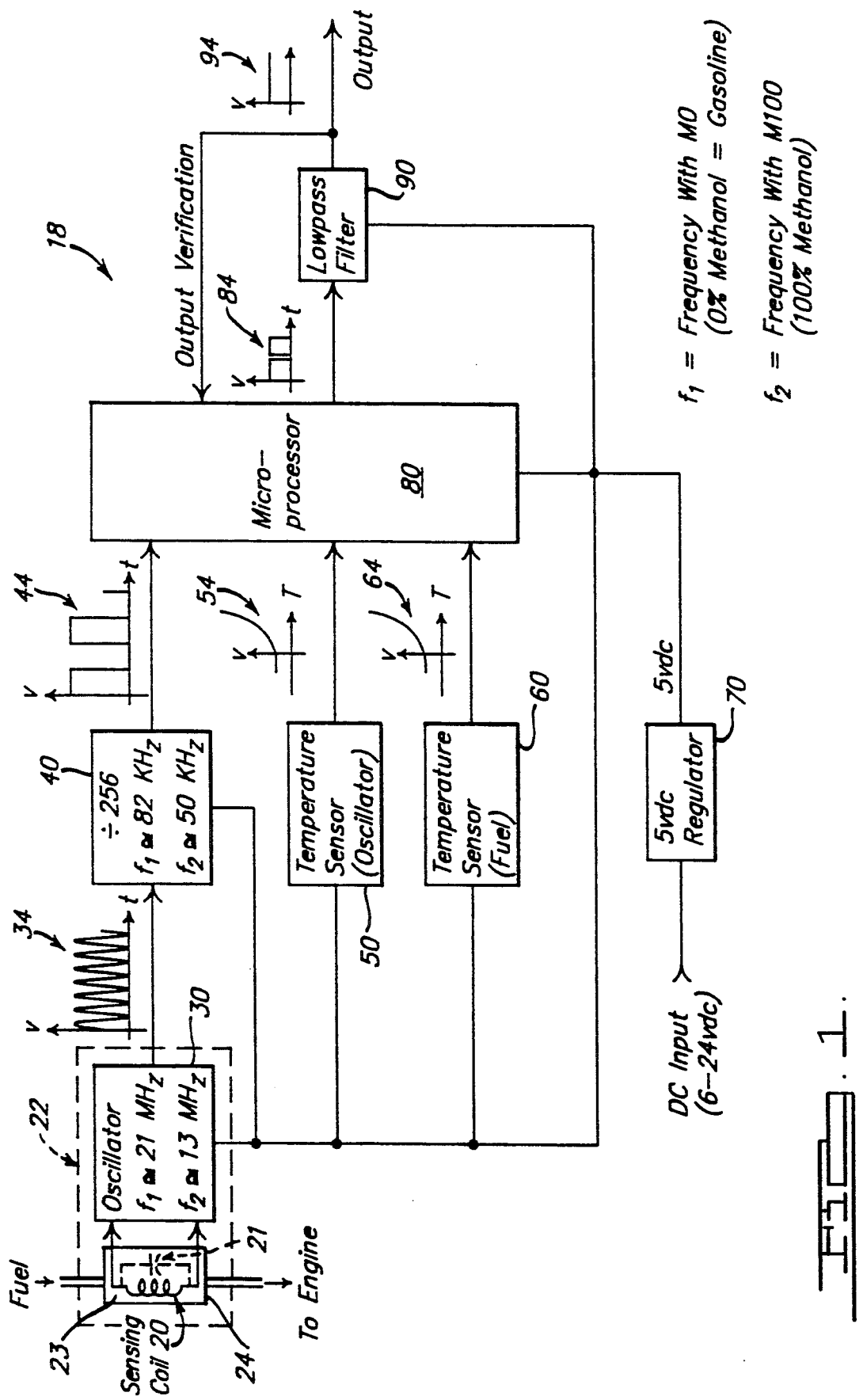
FIG. 1 is a functional block diagram showing the flexible fuel sensor and how it is interconnected to control circuitry and hardware related to the engine of a vehicle.

Referring to FIG. 1, the main elements of the subject invention are schematically shown. Fuel mixture sensing device 22 includes a cylindrical coil 20 fabricated from magnetic wire which is insulated with a polyamidimide coating. The polyamidimide coating provides a long life resistance to gasoline and alcohol fuels while providing the thinnest coating possible. Additionally, the coating is needed to eliminate shunt resistance (being generated between the loops of wire that form the coil) and fluid ion mobility effects (i.e., the conductivity of the fluid itself), yet it must still be thin enough so as not to mask the dielectric constant of the mixture being measured.

Coil 20 is preferably constructed by winding a 20 gauge magnetic wire in a 0.375" diameter coil. 22½ turns of wire produce a coil having the desired characteristics when the coil is approximately 0.81" long. Coil 20 has an inductance of approximately 2 $\mu$Henries.

Coil 20 is shown immersed in a fluid mixture 23 flowing through a cylindrical casing or coil chamber 24. The fuel is pumped from an automotive fuel tank (not shown) to a vehicle's engine (not shown). It is to be appreciated that the coil 20 could be directly immersed in the fuel tank. Coil chamber 24 is provided with input and output ports whereby the mixture 23 can flow there through. In an internal combustion engine application, mixture 23 would consist of a fuel mixture of gasoline and methanol and would flow through coil chamber 24 prior to delivery to the engine's fuel delivery system. It is contemplated that sensor 22 could be installed anywhere within or between the fuel tank and the fuel rail of conventional motor vehicles.

The ends of sensing coil 20 are connected to an electrical circuit 30. Preferably, circuit 30 is interfaced with coil 20 immediately adjacent to coil chamber 24 to minimize the length of interconnections and any resultant parasitic changes to the inductance or capacitance of the circuit. A preferred configuration of the apparatus according to the subject invention is illustrated in greater detail in reference to FIG. 4.

Coil 20 is energized via circuit 30, and a capacitance is generated between the loops of wire in coil 20 such that the loops of wire act as equivalent electrodes. The capacitance between two electrodes may be defined for measurement purposes as the charge stored per unit potential difference between them. Capacitance is dependent on the area, spacing, and the character of the dielectric material between the electrodes as shown in the formula below:

$$\text{CAPACITANCE} = (k)(A)/d$$

where "k" is the dielectric constant, "A" is the area circumscribed by the loops of wire which form the equivalent electrodes, and "d" is the distance between the electrodes. We are only concerned here with the dielectric constant of the mixture since the area and the spacing will remain constant.

Dielectric materials are electrical insulators in which an electrical field can be sustained with a minimum dissipation of power. The fluid with the higher dipole moment will have the higher dielectric constant. In a mixture of two known fluids, a proportional relationship exists between the percentage of each fluid in the mixture and its cumulative dielectric constant. This also means that capacitance will increase with an increase in percentage of the fluid possessing the higher dielectric constant. It is this relationship which the subject invention exploits.

Coil 20 is electrically interfaced with circuit 30. In fact, coil 20 is used as the resonant element in an oscillator for generating a resonant frequency which is related to the amount of one of the fluids (methanol in the preferred embodiment) present in the fuel mixture. The oscillator portion of circuit 30 drives coil 20 until the resonant frequency of the coil is determined. The oscillator is a tuned input type using coil 20 and its distributed capacitance as a parallel resonant tank circuit which causes oscillation at the tank's resonant frequency. The change in dielectric constant therefore, causes a change in the resonant frequency. In this manner, resonant frequency decreases as capacitance increases according to the formula:

$$f = \frac{1}{2\pi \sqrt{(LC)}}$$

and $$C = C_0(k + \epsilon_{fl})$$

where "f" is frequency, "L" is the inductance of sensing coil 20, "C" is Capacitance, $\epsilon_{fl}$ is the relative dielectric constant of the fluid being measured, $C_0$ is the base distributed capacitance of the sensing coil, and k is a multiplier for the effects of coil insulation and oscillator circuitry and includes all stray or parasitic impedances reflected across the inductor terminals.

This shows that $C_0k$ represents the free air capacitance of the coil and oscillator and chamber (and associated housing, etc.; i.e.: without the effects of the fluid) and $C_0k + C_0\epsilon_{fl}$ represents the free air capacitance and that of the coil in the fluid.

From the above relationships, it can be seen that as the percentage of the fluid with the higher dielectric constant increases, the resonant frequency of coil 20 immersed within the mixture decreases. As will be detailed hereinafter, the circuit 30 converts the frequency to a voltage and employs the voltage signal as an output.

Further reference to FIG. 1 illustrates the subject invention as applied to an alcohol/gasoline mixture, and more preferably a methanol/gasoline fuel mixture for an internal combustion engine. The output signal from circuit 30 is sent to a microprocessor 80 which, in turn, selectively adjusts the spark timing and fuel ratio of engine (not shown) of a vehicle (also not shown) for proper internal combustion.

However, it should be understood that the subject invention embodies the novel concept of measuring changes in the resonant frequency of a tank circuit comprising a coil with its inherent distributed capacitance immersed in a fluid mixture to determine the combined dielectric constant of the mixture. In this manner, the specific value, number and interconnection of components disclosed herein are presented to illustrate a preferred embodiment and are not to be construed to limit the invention accordingly. Furthermore, design considerations affecting the final configuration of coil 20 will likewise affect the component values required for proper circuit operation.

FIG. 1 generally shows a functional block diagram of the subject flexible fuel sensor system 18. All of the electrically powered blocks shown in FIG. 1 are powered from a DC input of between 6-24 Volts DC through a 5 V DC regulator 70.

The sensing coil 20 shown is a part of the oscillator circuit 30. Together, the sensing coil 20 and the rest of the oscillator circuit 30 form the flexible fuel sensor 22 shown set off with dashed lines. The flexible fuel sensor output signal is shown as 34.

The sensing coil 20 is in direct communication with the fluid to be sensed. In the case of the preferred embodiment more specifically shown and described herein, the fluid to be sensed is a methanol fuel mixture (fuel) 23 shown in a reservoir or coil chamber 24. The sensing coil 20 can be in a fuel tank, remote from the rest of the oscillator circuit 30 or could be configured to sense a sample of fuel 23 and immerse the coil 20 into coil chamber 24 remote from the fuel tank. In either event, the sensing coil 20 must be in direct communication with the fuel 23.

The flexible fuel sensor 22 can be set to oscillate at any frequency, however for purposes of the subject invention, the flexible fuel sensor output signal 34 oscillates in a range of frequencies between 13 MHz and 21 MHz was chosen. This frequency range is a function of the size of the sensing coil 20 and of the characteristics of the fluid or fuel to be sensed.

The flexible fuel sensor output signal 22 is fed into a divide by ($\div$) 256 circuit shown at 40 in FIG. 1. This circuit is a function of the particular electronics system used with the flexible fuel sensor 22 and may not be needed with other circuitry. Similarly, the system 18 can be reproduced using combinations of discrete electronic components. The divide by 256 circuit 40 converts the flexible fuel sensor output signal 34 to a frequency ranging between 50 KHz and 82 KHz. The flexible fuel sensor output signal 34 appears as divided flexible fuel sensor output signal 44 from the output of block 40. This divided flexible fuel output signal 44 is presented to microprocessor 80 for further analysis which will be explained below.

Oscillator temperature sensor 50 generates a oscillator temperature sensor output signal 54 which is a function of the temperature of the oscillator 30 itself. In the case of the preferred embodiment shown and described herein, the oscillator temperature sensor output signal 54 is a voltage. The oscillator temperature sensor output signal 54 is also presented to the microprocessor 80 for processing with the divided flexible fuel sensor output signal 44. This also will be explained more fully below.

The preferred embodiment of the system 18 also includes a fuel temperature sensor 60 which, as in the case of the oscillator temperature sensor 50, generates a voltage output. This is shown as fuel temperature sensor output signal 64 and is a function of the temperature of the fuel 23 being sensed. It also is processed by the microprocessor 80.

Microprocessor 80 compares the divided flexible fuel sensor signal 44 along with the oscillator temperature sensor signal 54 and the fuel temperature sensor signal 64 to predetermined tables and/or curves of empirical data to determine the methanol concentration of the sensed fuel 23. This information is contained in the microprocessor output signal 84.

A low pass filter 90 is also provided to convert the pulse width modulated microprocessor output signal 84 back to an analog voltage output 94. The information in either signal 84 or 94 can be used for display purposes or sent to an engine computer (not shown) to change appropriate sections of the operating characteristics of the engine in response and correlated to the concentration of methanol in the fuel 23. Output verification is also provided by feeding the signal 94 back to microprocessor 80 for comparison. This is a matter of design choice and may not be necessary for a particular implementation of the circuitry and system described and claimed herein; in the example shown, it is more of a development tool. Output protection can be provided for production versions of this circuit.

Figure 2:
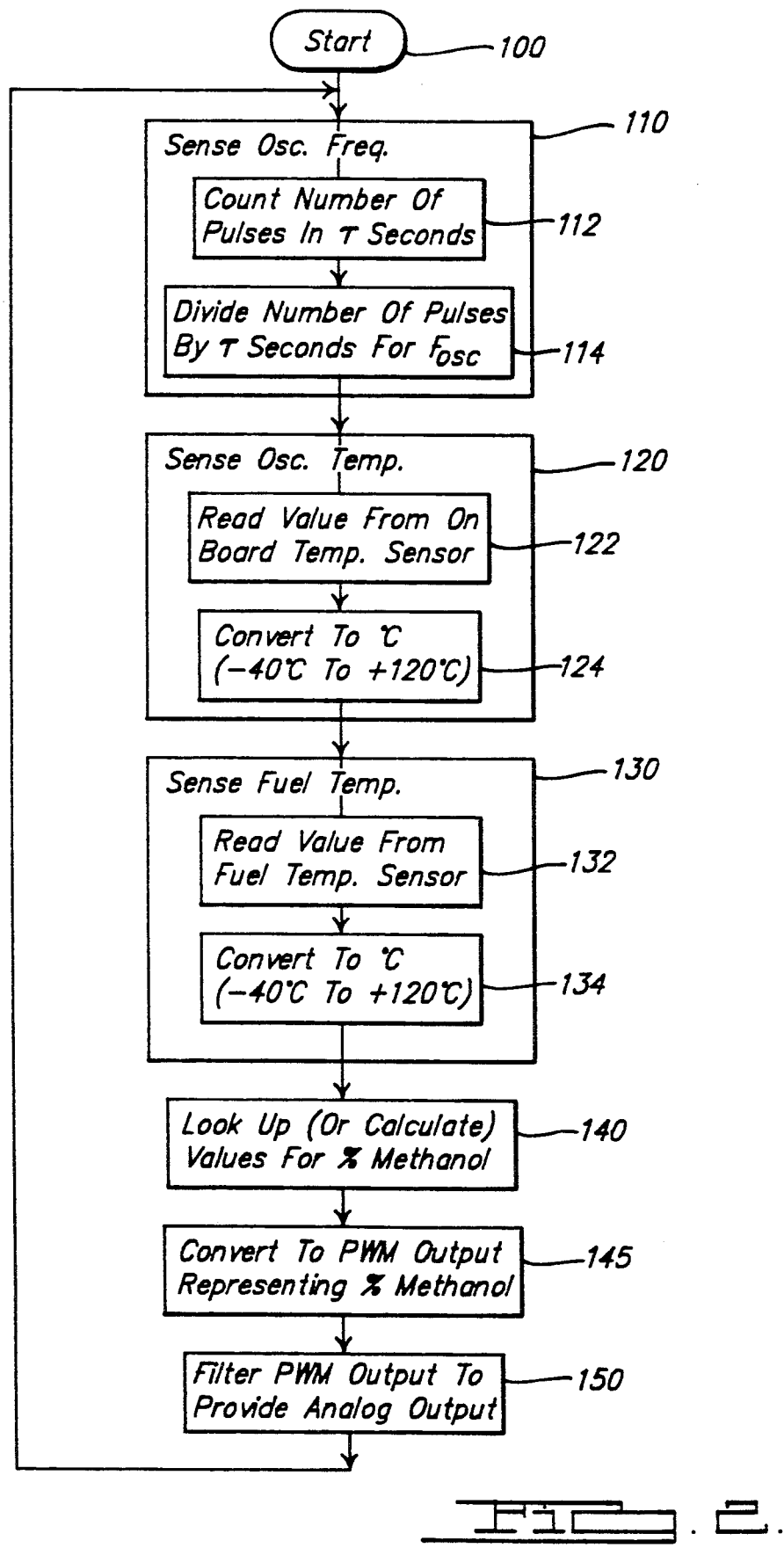
FIG. 2 is an overall flow chart of the methodology employed by the flexible fuel system described herein to detect the composition of the fuel sampled.

Referring now to FIG. 2, an overall flow chart is provided to show a method of sensing the percent methanol in fuel utilizing the system 18 shown in FIG. 1.

The method starts in block 100 and is called for by the system 18 either on a periodic basis or on an interrupt basis as needed.

Next, in blocks 110, 120, and 130 the system 18 calls for and senses the frequency output of the sensor 22, the temperature of oscillator 30, and the temperature of the fuel 23.

Then in blocks 140 and 150, the system 18 uses the information from blocks 110, 120 and 130 to look up in the memory in microprocessor 80 or calculate in microprocessor 80 the % methanol. It is a PWM modulated output and is proportional to % methanol (10%-90%) duty cycle. The output of the system 18 will be a temperature compensated value that corresponds to the % methanol in the fuel sensed using the fuel sensor 22.

The look up data in memory can be empirically derived by measuring the dielectric constant of various known concentrations of gasoline and methanol. Real time computation can also be accomplished with mathematical models of the relationship between the dielectric constant measured and the concentration of methanol in the fluid fuel) mixture.

Next the microprocessor 80 calls for the method to return to repeat the method beginning with block 110 the next time it is required.

More specifically, the steps that the system 18 uses to convert the sensed voltages from sensors 22, 50 and 60 are further described in FIG. 3 and illustrates a more detailed methodology to that described in conjunction with FIG. 2.

One way to sense the frequency of the flexible fuel sensor 22 is shown in blocks 112 and 114. In block 112, the microprocessor 80 counts the number of pulses on the output of Oscillator 30 in the time period of $\tau$ seconds. Then in block 114, the microprocessor 80 divides the number of pulses sensed in block 112 by $\tau$ to get the frequency of the output from flexible fuel sensor 22.

Blocks 122 and 124 in FIG. 3 correspond to block 120 in FIG. 2. In order to sense the temperature of oscillator 30 in block 120, the microprocessor 80 will read values from the on board temperature sensor 50. The output from the particular sensor 50 used in this application is calibrated in the range from 0-5 volts. Then in block 124, the voltage output from temperature sensor 50 will be converted to a temperature for use in computation or memory table look up steps by microprocessor 80. The conversion will be in the range of ($-40°$ C. to $+120°$ C.). This conversion is retained in the memory of microprocessor 80.

Similar sense and conversion steps are performed in blocks 132 and 134 in FIG. 3 which correspond with the sensing of the fuel temperature in block 130 in FIG. 2. More specifically, in block 132 the microprocessor 80 will read the voltage output from the fuel temperature 60 which for the particular sensor 50 used is calibrated from 0 to 5 volts. The conversion to a temperature value that can be used by microprocessor 80 for compensatory computation/look up purposes later in the methodology, is done in block 134 in the range of ($-40°$ C. to $120°$ C.).

Figure 3B:
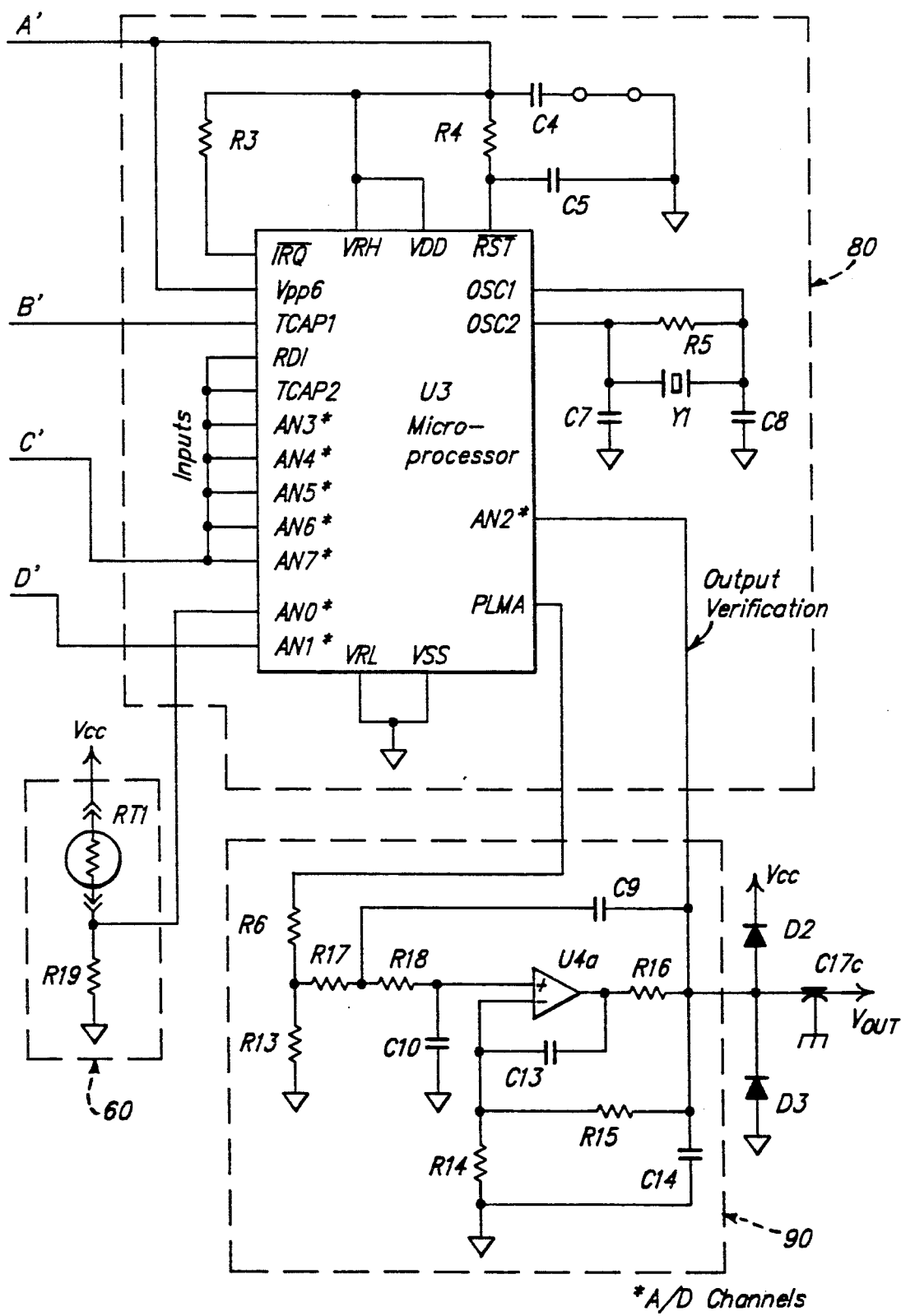
FIG. 3B is a continuation of the schematic diagram of the flexible fuel system shown in FIG. 3A.

Referring to FIG. 3A and to FIG. 3B, presented is a schematic diagram of the circuitry of the flexible fuel sensor system 18 as shown in block form in FIG. 1.

All of the electrically powered components shown are powered from a DC input of between 6 and 24 volts D.C. through a 5 volt DC Regulator 70. The heart of this regulator is a regulator chip U5. Several commercially available components are available to accomplish this function. This particular chip in the preferred embodiment employs a capacitive network made up of feed-through filter capacitors C17a and C17b to limit radio frequency interference, input filter capacitor C11 for smoothing ripple of the voltage signal supplied by VIN (6-24 volts) and output filter capacitor C12 for stability and ripple rejection on the output of regulator chip U5. The VIN represents voltage available from the supply system in an automotive electrical power system (not shown). The resultant output from the regulator 70 is a 5 Volt D.C. which is labelled Vcc.

The sensing coil 20 is a part of the oscillator circuit 30 as previously shown in FIG. 1. Together, the sensing coil 20 and the rest of the oscillator circuit 30 form the flexible fuel sensor 22.

Upper bias resistor R1 and Lower bias resistor R2, along with coupling capacitor C6 and sensing coil 20 form the input network to the rest of the oscillator circuit 30. Invertor/Amplifiers U1a, U1b and U1c form the heart of the oscillator operation along with feedback resistor R20 across U1a, feedback capacitor C1 across the output of U1b and the input to U1a, and bypass filter capacitor C2.

In operation, the sensing coil 20 is in direct communication with the fuel 23 (see FIG. 1) which in the preferred embodiment is the fluid to be sensed. The sensor 22 can be set to oscillate at any frequency but for purposes of the subject invention (to sense the concentration of methanol in the fuel), the sensor produces an output 34 (see FIG. 1) with a frequency range between 13 MHz and 21 MHz.

The frequency of oscillation is determined by the coil L (shown as 20 in the figures) and its distributed capacitance C (shown as 21 in the figures). The oscillator 30 can be described as a tuned input oscillator where L and C form a parallel resonant tank circuit.

From feedback theory it is known that a requirement for oscillation is a loop gain greater than or equal to unity along with zero or 360 degrees of phase shift around the loop. The gain for this oscillator is provided by two unbuffered high speed CMOS inverters (U1a and U1b). Using a CMOS device in a standard hex package promotes thermal stability due to the complementary nature of the device. This reduces the propagation delay and input capacitance of the devices for better operation at the frequencies of interest.

The capacitor C1 serves as a feedback element in the circuit, providing positive feedback to promote regeneration and oscillation at the resonant frequency. C2 provides a ground path for the AC voltage developed across the coil while still allowing a DC bias set by R1 and R2 to exist at the input of U1a.

Resistor R20 provides some negative feedback on the first amplifier stage (U1a) in order to reduce its gain and flatten its transfer characteristic. This ensures that the oscillator will start under all conditions and helps to eliminate component variability.

C3 is provided to AC couple the enclosure around the sensing coil 20 (and related circuitry) to the circuit ground. This has a two-fold effect. It decreases the effective distributed capacitance $kC_0$ of the sensing coil 20 and allows more of a frequency shift to occur when changing the dielectric fluid in the chamber, and it provides shielding to prevent RF radiation from the circuit by shunting the eddy currents generated in the enclosure to circuit ground. It is not DC coupled so that varying ground potentials on the enclosure will not cause variations in the circuit's ground potential.

The output from U1b is then fed through U1c to isolate and buffer the oscillator output from any loads placed on it. The high frequency output is obtained at the output of U1c.

It is also important to use standard practice and place a bypass capacitor C4 across the power supply to U1 to bypass any high frequency switching currents and prevent them from infiltrating the supply lines.

The capacitance of the tank circuit is determined by several factors which can be accounted for by the following formula:

$$C = C_0(k + \epsilon_{fl});$$

where:
C is the distributed capacitance of the tank circuit;
$C_0$ is the distributed capacitance of the coil free standing in a vacuum with no insulation;
k is a constant which includes the effects of the insulation on the wire the effects of the housing and the input impedance of the amplifier and bias network;
$\epsilon_{fl}$ is the dielectric constant of the fluid being sensed;
$kC_0$ is the effective distributed capacitance of the tank circuit;

$\epsilon_f C_0$ is the additional capacitance determined by the dielectric constant of the fluid.

The output signal 34 is fed into a divide by 256 circuit 40. Except for a bypass filter capacitor C3 and some connections between various pins as shown in FIG. 3A, the circuit comprises a binary ripple counter U2 which is commercially available as a IC number 74HC393 (any 8 bit counter will work to divide by 256). As shown in FIG. 1, the output of the divide by 256 circuit 40 is the divided flexible fuel sensor output signal 44. The divide by 256 circuit 40 converts the flexible fuel sensor output signal 34 to a frequency ranging between 50 KHz and 82 KHz. The signal 44 is presented to microprocessor 80 along with the signals from the oscillator temperature sensor 50 and the fuel temperature sensor 60.

Oscillator temperature sensor 50 generates an output signal 54, as shown in FIG. 1, which is a function of the temperature of the oscillator 30 itself. The output 54 is in the form of a voltage. The sensor 50 comprises bias thermistor RT2 and voltage divider resistor R11. The choice of this temperature sensor is directed by parameters that are not necessarily unique to the flexible fuel sensor system described and claimed herein; many other types of temperature sensors would work.

Fuel temperature sensor 60 generates an output signal 64, as shown in FIG. 1, which is a function of the temperature of the fuel 23 (in coil chamber 24 or in the fuel system (not shown)). The output 64 is also in the form of a voltage. The sensor 60 comprises divider resistor R7 which works with the thermistor RT1. The choice of this temperature sensor is directed by parameters that are not necessarily unique to the flexible fuel sensor system described and claimed herein; many other types of temperature sensors would work.

Microprocessor 80 compares the divided flexible fuel sensor signal 44 along with the oscillator temperature sensor signal 54 and the fuel temperature sensor signal 64 to predetermined tables and/or curves of empirical data to determine the methanol concentration of the sensed fuel 23. This comparison information is contained in the microprocessor output signal 84.

The heart of the microprocessor 80 circuit is microprocessor chip U3 which is a commercially available chip, such as a MC68HC05B4, MC68HC05B6, MC68HC805B6, or MC68HC705B5 with the interconnections as shown. The chip U3 contains a memory (not shown) in which is stored the predetermined relationships which allow the comparison of the sensed fuel to be compared with known characteristics of the concentrations of methanol in the fuel. This process is described in detail with respect to the method shown in FIG. 2.

The chip U3 is shown in FIG. 3B along with the external components as necessary: pull up resistors R3 and R4, filter capacitor C4, reset capacitor C5, clock shunt resistor R5 and clock capacitors C7 and C8, and crystal resonator Y1.

A low pass filter 90 converts the pulse width modulated microprocessor output signal 84 back to an analog voltage output 94, shown in FIG. 1. The information in either signal 84 or 94 can be used for display purposes or sent to an engine computer (not shown) to change appropriate sections of the operating characteristics of the engine in response and correlated to the concentration of methanol in the fuel 23. Output verification is also provided by feeding the signal 94 back to microprocessor 80 for comparison. This is a matter of design choice and may not be necessary for a particular implementation of the circuitry and system described and claimed herein; in the example shown, it is more of a development tool. Output protection can be provided for production versions of this circuit.

More specifically, low pass filter 90 comprises a voltage divider comprising resistors R6 and R13, input resistor R17, resistor R18, feedback capacitor C9 and capacitor C10 along with amplifier U4a, and feedback capacitor C13. In addition, resistor R16, feedback resistor R15, gain control resistor R14, and filter capacitor C14 are provided along with output clamping diodes D2 and D3 to complete the low pass filter design. This is a 2nd order Butterworth low pass filter of conventional design and others would also work.

Capacitor C16 is provided to AC couple the enclosure to the sensor ground and output filter capacitor C17c is provided to limit radio frequency feed through interference on the output.

Figure 4:
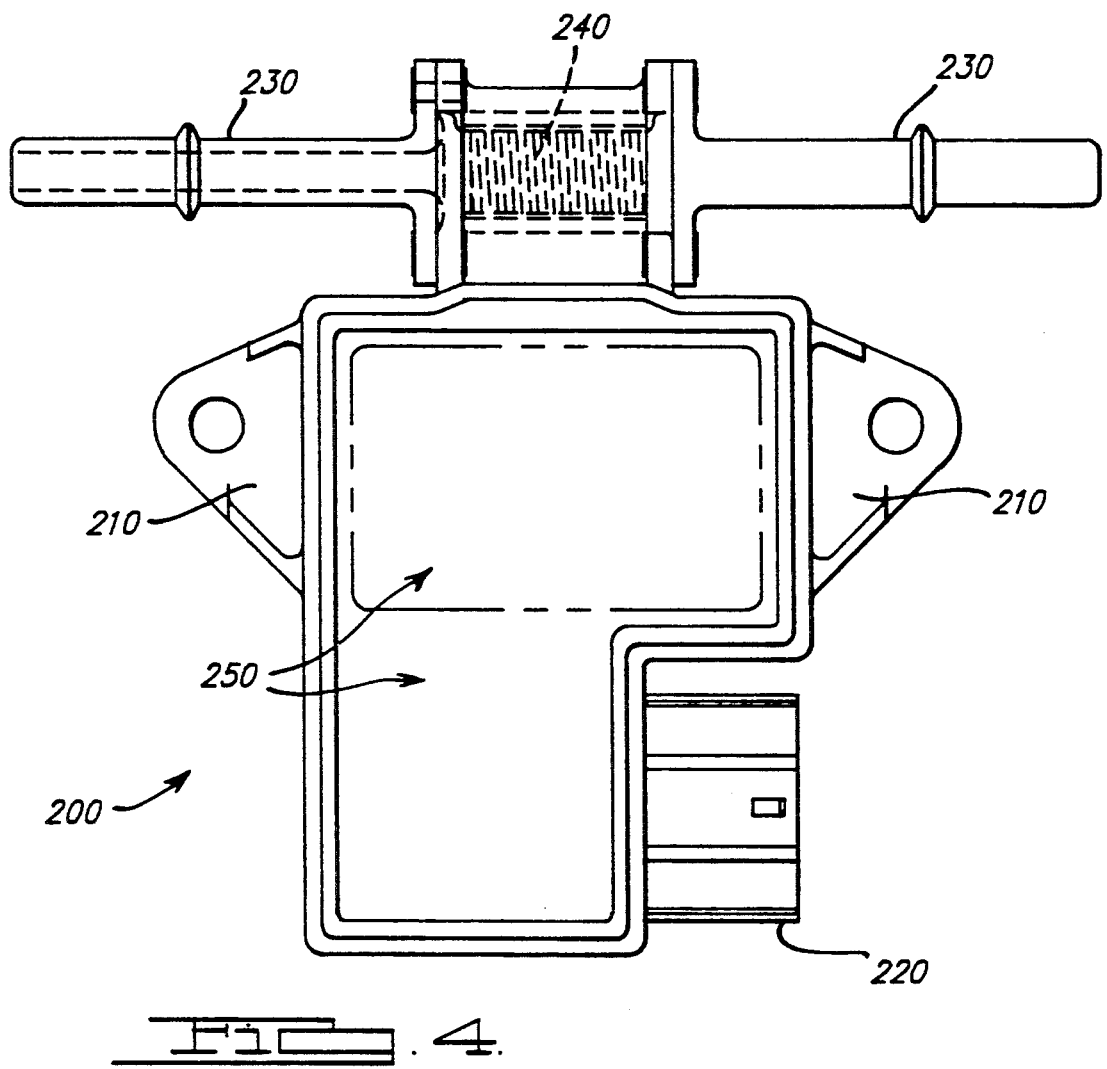
FIG. 4 is top view of the housing in which the flexible fuel sensor is mounted.
Figure 5:
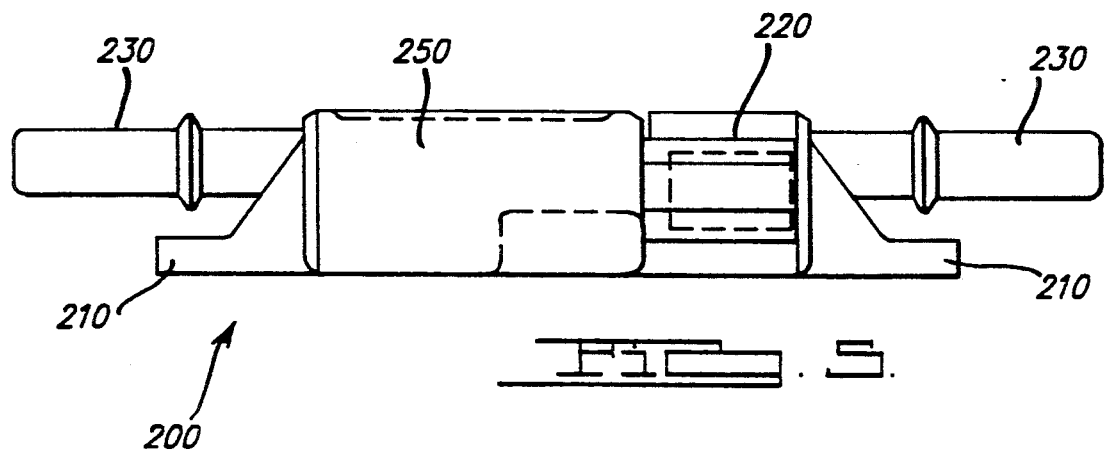
FIG. 5 is a side view of the housing shown in FIG. 4.

Referring now to FIGS. 4 and 5, shown is housing 200 which, in cavity 250, encloses a circuit board (not shown) carrying the components of the system 18 described herein. The housing is provided with flanges 210 for use with mounting hardware to secure it to a suitable location on the vehicle. Also provided is a connector means 220 to allow for the electrical interconnection between the circuit board carrying the subject system circuitry and the rest of the vehicle's engine control hardware. Fuel inlet/outlets 230 are also provided to communicate with fuel line tubing (not shown) which will transport fuel 23 to and from the inlet/outlets 230 which in turn allow the sensing coil 22 (also shown as coil bobbin 240 in FIG. 4) to interact with the fuel 23.

Figure 6:
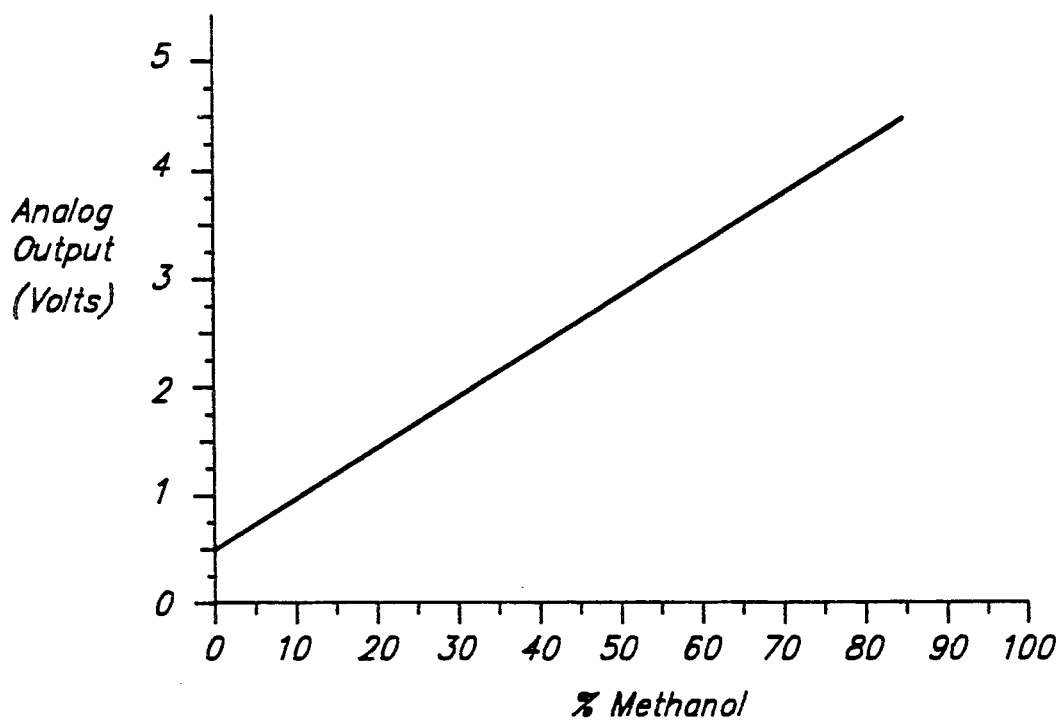
FIG. 6 is a graph of the analog output signal from the flexible fuel sensor system vs. the percentage methanol sensed in the fuel.
Figure 7:
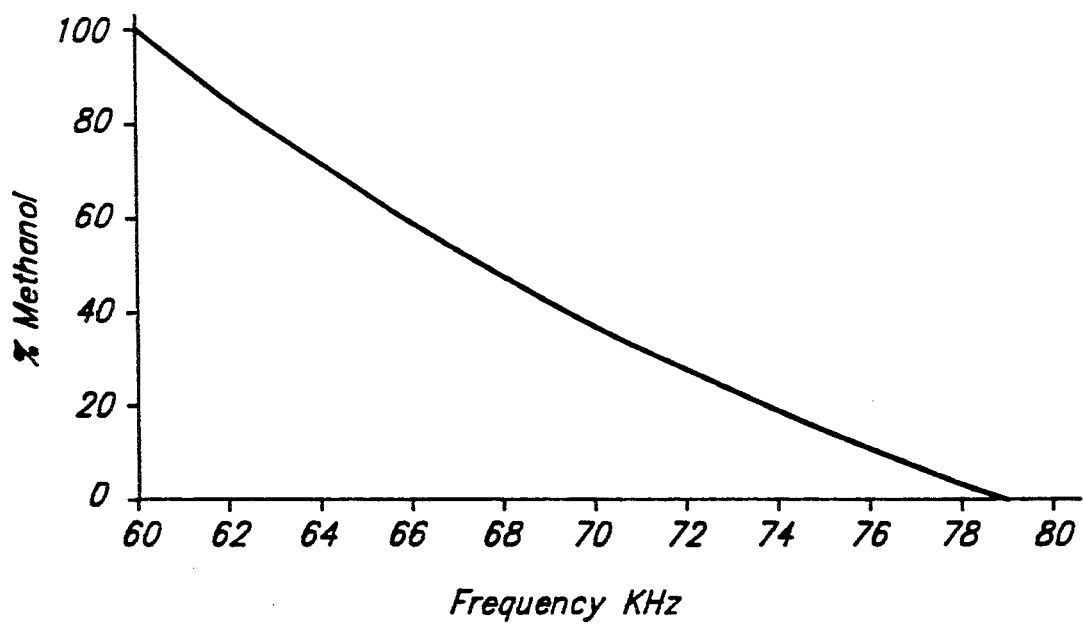
FIG. 7 is a graph of the percentage methanol sensed in the fuel vs. the frequency output of the flexible fuel sensor.

Referring now to FIG. 6 shown is a graph of the analog output signal from the flexible fuel sensor system vs. the percentage methanol sensed in the fuel. FIG. 7 shows a graph of the percentage methanol sensed in the fuel vs. the frequency output of the flexible fuel sensor. These two curves are merely representative of the approximate relationship between the voltage and frequency outputs as related to the percentage methanol contained in the fuel 23. The shapes of the curves will change slightly depending on the scale used and the choice of the hardware used, the amount of fuel present to sense, the temperatures involved, etc.

It should be understood that while this invention has been discussed in connection with one particular example, those skilled in the art will appreciate that other modifications can be made without departing from the spirit of this invention after studying the specification, drawings and the following claims.

I claim:

1. A method of controlling preselected parameters in an engine utilizing a fuel mixture of first and second liquids wherein the first and second liquids respectively have first and second dielectric constants, the method comprising:

immersing an inductive element into the fuel mixture such that the mixture at least partially determines a value of distributed capacitance of the inductive element in accordance with the first and second dielectric constants, the inductive element and its distributed capacitance forming a resonant tank circuit of an oscillator which generates a signal whose frequency is determined by the distributed capacitance;

detecting the frequency of the oscillator generated signal;

determining percentages of the first and second fluids in the fuel mixture as a function of the oscillator frequency; and utilizing the percentages of the first and second liquids in the fuel mixture to control the preselected engine parameters.

2. The method of claim 1 where the step of detecting the frequency of the inductive element further comprises:

counting a number of pulses generated by the oscillator generated signal in a predetermined time period; and dividing the number of pulses by the predetermined time period to obtain the frequency.

3. The method of claim 2 further comprising compensating the frequency obtained as a function of temperature of the fuel.

4. The method of claim 2 further comprising compensating the frequency obtained as a function of temperature of the oscillator.

5. The method of claim 2 further comprising compensating the frequency obtained as a function of temperature of the fuel and temperature of the oscillator.

6. The method of claim 1 where the step of determining the percentages of the fluids in the mixture as a function of the oscillator frequency includes comparing frequency values for known fluid mixtures with the frequency values for the fuel mixture.

* * * * *